(12) United States Patent
Bagley et al.

(10) Patent No.: US 7,834,994 B2
(45) Date of Patent: *Nov. 16, 2010

(54) SENSORS FOR DYNAMICALLY DETECTING SUBSTRATE BREAKAGE AND MISALIGNMENT OF A MOVING SUBSTRATE

(75) Inventors: William A. Bagley, Tokyo (JP); Paohuei Lee, San Jose, CA (US); Kyung-Tae Kim, Suwon (KR); Sam-Kyung Kim, Kumi (KR); Toshio Kiyotake, Hyogo (JP); Sam Kim, San Ramon, CA (US); Takayuki Matsumoto, Santa Clara, CA (US); Jonathan Erik Larson, East Palo Alto, CA (US); Makoto Inagawa, Palo Alto, CA (US); James Hoffman, San Jose, CA (US); Billy C. Leung, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/255,629

(22) Filed: Oct. 21, 2008

(65) Prior Publication Data
US 2009/0050270 A1 Feb. 26, 2009

Related U.S. Application Data

(63) Continuation of application No. 10/973,116, filed on Oct. 26, 2004, now Pat. No. 7,440,091.

(51) Int. Cl.
*G01N 21/00* (2006.01)
(52) U.S. Cl. .................................. 356/237.2
(58) Field of Classification Search ............. 356/213, 356/600, 399, 237.2, 400, 638, 639, 237.5
See application file for complete search history.

(56) References Cited

U.S. PATENT DOCUMENTS 4,153,367 A 5/1979 Lietar et al.

(Continued)

FOREIGN PATENT DOCUMENTS

EP 0891840 1/1999

(Continued)

OTHER PUBLICATIONS

PCT International Search Report and Written Opinion for PCT/US06/01724, Dated Nov. 20, 2006 (APPM/009058.PCT).

(Continued)

*Primary Examiner*—Tarifur Chowdhury
*Assistant Examiner*—Jonathan M Hansen
(74) *Attorney, Agent, or Firm*—Patterson & Sheridan, LLP

(57) ABSTRACT

An apparatus and method incorporating at least two sensors that detect the presence of a substrate is provided. In one embodiment, a method for transferring a substrate in a processing system is described. The method includes positioning a substrate on an end effector in a first chamber, moving the substrate through an opening between the first chamber and a second chamber along a substrate travel path, and sensing opposing sides of the substrate travel path using at least two sensors positioned proximate to the opening, each of the at least two sensors defining a beam path that is directed through opposing edge regions of the substrate when at least a portion of an edge region traverses the beam path.

29 Claims, 7 Drawing Sheets

U.S. PATENT DOCUMENTS

| | | | |
|---|---|---|---|
| 4,819,167 A * | 4/1989 | Cheng et al. ............... 700/59 |
| 5,452,521 A | 9/1995 | Niewmierzycki |
| 5,483,138 A * | 1/1996 | Shmookler et al. ..... 318/568.16 |
| 5,563,798 A | 10/1996 | Berken et al. |
| 5,917,601 A * | 6/1999 | Shimazaki et al. .......... 356/622 |
| 5,980,194 A | 11/1999 | Freerks et al. |
| 6,120,601 A | 9/2000 | Landau et al. |
| 6,190,037 B1 | 2/2001 | Das et al. |
| 6,215,897 B1 | 4/2001 | Beer et al. |
| 6,235,634 B1 | 5/2001 | White et al. |
| 6,294,296 B1 | 9/2001 | Weigl et al. |
| 6,327,517 B1 | 12/2001 | Sundar |
| 6,339,730 B1 | 1/2002 | Matsushima et al. |
| 6,356,346 B1 | 3/2002 | Hagen et al. |
| 6,502,054 B1 | 12/2002 | Mooring et al. |
| 6,556,807 B1 | 4/2003 | Horie et al. |
| 6,556,887 B2 | 4/2003 | Freeman et al. |
| 6,577,923 B1 | 6/2003 | White et al. |
| 6,629,053 B1 | 9/2003 | Mooring |
| 6,684,123 B2 | 1/2004 | Jevtic et al. |
| 6,856,858 B2 * | 2/2005 | Kurita ..................... 700/218 |
| 7,039,501 B2 * | 5/2006 | Freeman et al. ............ 700/258 |
| 2001/0024609 A1 | 9/2001 | White et al. |
| 2002/0021959 A1 | 2/2002 | Schauer et al. |
| 2002/0111710 A1 | 8/2002 | Perlov et al. |
| 2003/0012631 A1 | 1/2003 | Pencis et al. |
| 2003/0014155 A1 | 1/2003 | Pencis et al. |
| 2003/0083776 A1 | 5/2003 | Schauer et al. |
| 2003/0117680 A1 | 6/2003 | Allen et al. |
| 2003/0132746 A1 | 7/2003 | Cox |
| 2003/0149947 A1 | 8/2003 | Sarig |
| 2003/0154002 A1 | 8/2003 | Lappen et al. |
| 2003/0161706 A1 | 8/2003 | Kurita et al. |
| 2003/0179369 A1 | 9/2003 | Feldman et al. |
| 2003/0218741 A1 | 11/2003 | Guetta |
| 2003/0227618 A1 | 12/2003 | Some |
| 2004/0016896 A1 | 1/2004 | Almogy et al. |
| 2004/0055397 A1 | 3/2004 | Kurita |
| 2004/0067127 A1 | 4/2004 | Hofmeister et al. |
| 2004/0075068 A1 | 4/2004 | Feldman et al. |
| 2005/0046831 A1 * | 3/2005 | Chen ..................... 356/237.2 |

FOREIGN PATENT DOCUMENTS

EP     1102137     5/2001

OTHER PUBLICATIONS

Korean Office Action for Application No. 10-2008-7019851 dated May 31, 2010 (APPM/9058/KORS).

* cited by examiner

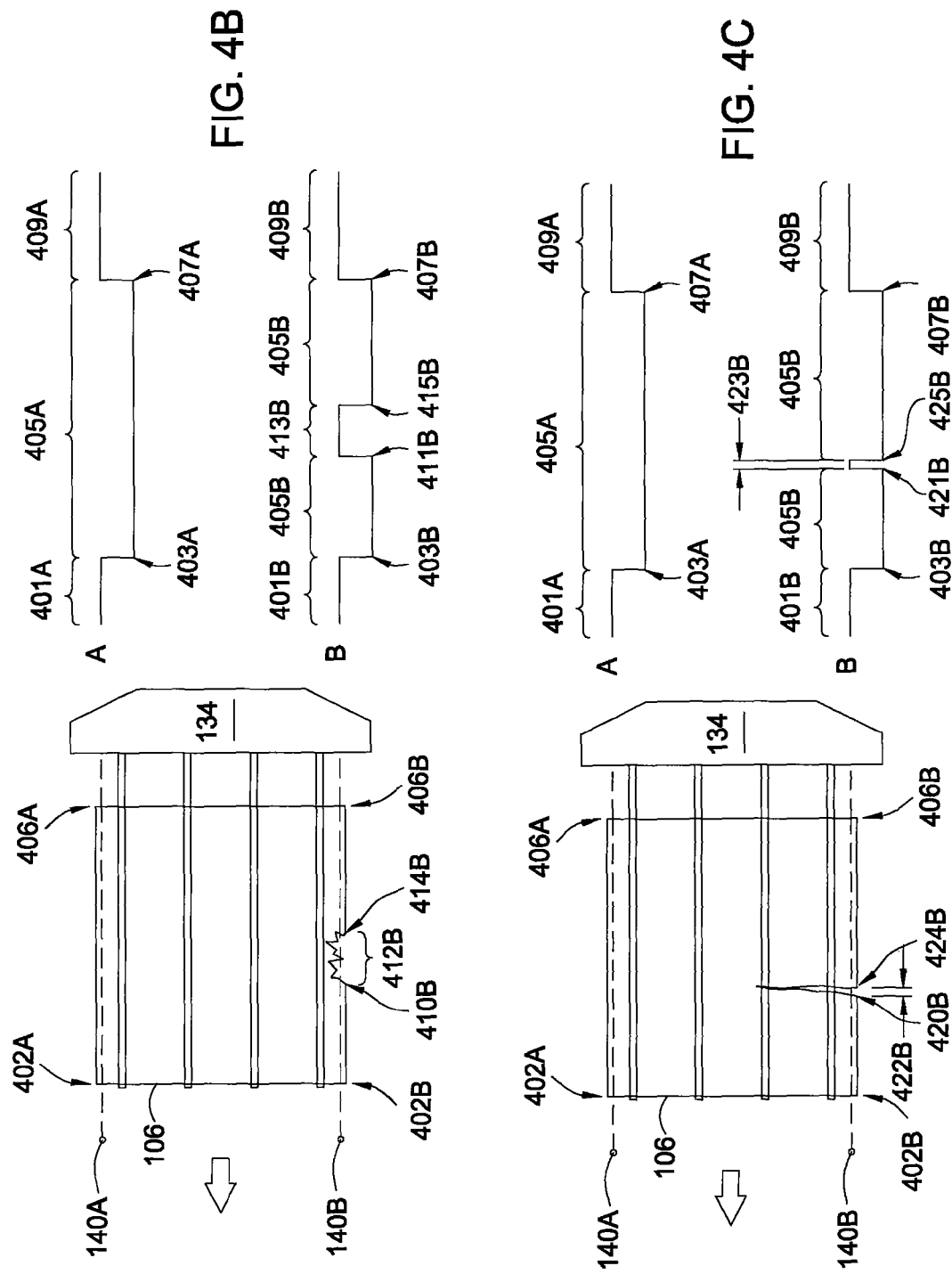

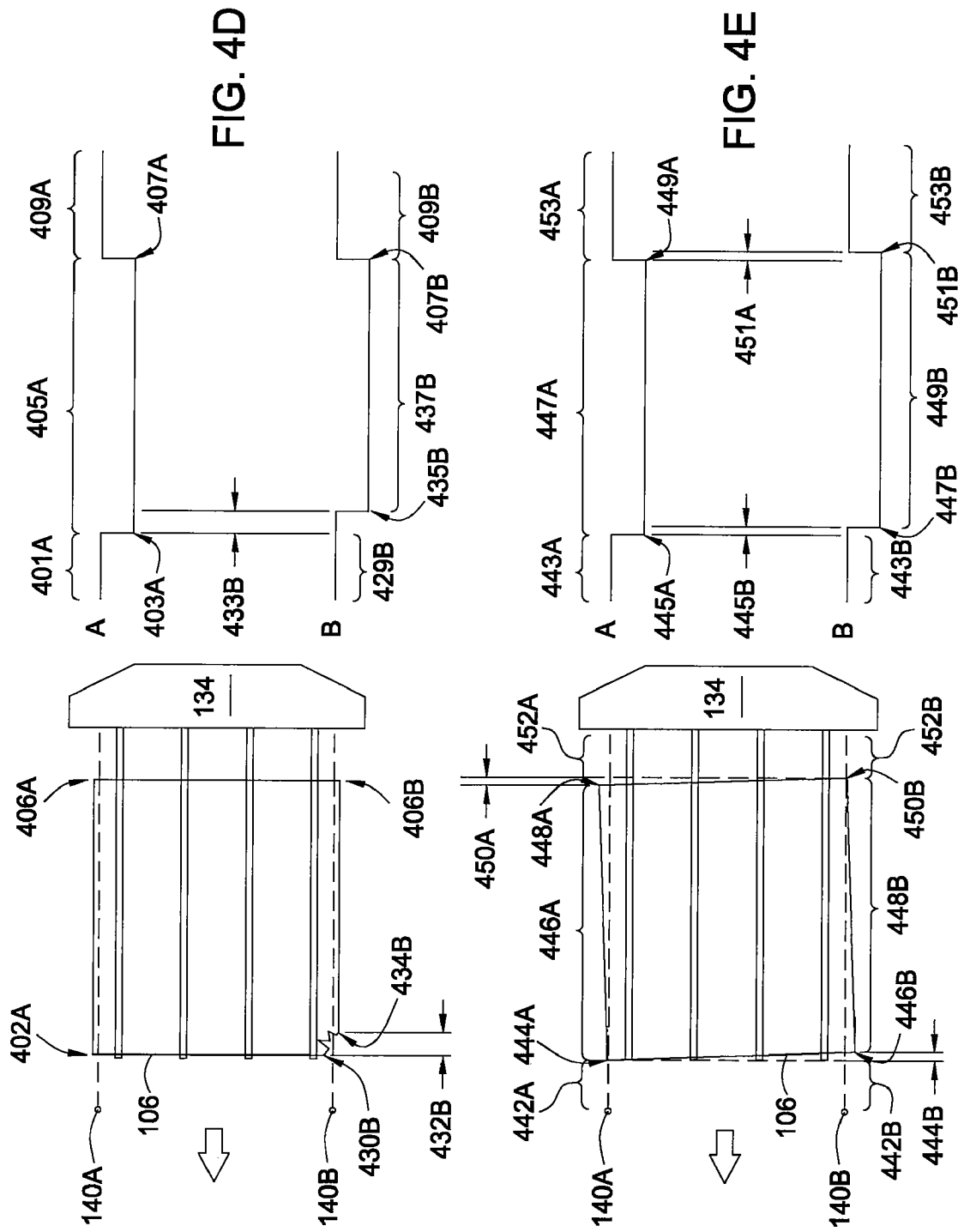

SENSORS FOR DYNAMICALLY DETECTING SUBSTRATE BREAKAGE AND MISALIGNMENT OF A MOVING SUBSTRATE

CROSS-REFERENCE TO RELATED APPLICATIONS

This application is a continuation of U.S. patent application Ser. No. 10/973,116, which was filed Oct. 26, 2004, and issued as U.S. Pat. No. 7,440,091 on Oct. 21, 2008, which is incorporated by reference in its entirety.

BACKGROUND OF THE INVENTION

1. Field of the Invention

Embodiments of the present invention generally relate to an apparatus and method for detecting substrate breakage and misalignment of a moving substrate in a continuous and cost-effective manner.

2. Description of the Related Art

Substrate processing systems are used to process substrates such as silicon wafers in the production of integrated circuit devices and glass panels in the manufacture of flat panel displays. Typically, one or more robots are disposed in the substrate processing system to transfer substrates through a plurality of process chambers for conducting a sequence of processing steps of the fabrication process. Generally, a substrate processing system includes a cluster tool having a centrally located transfer chamber, with a transfer chamber robot disposed therein, and a plurality of process chambers surrounding the transfer chamber. The transfer chamber is sometimes coupled to a factory interface that houses a factory interface robot and a plurality of substrate cassettes, each of which holds a plurality of substrates. To facilitate substrate transfer between a generally ambient environment within the factory interface and a vacuum environment within the transfer chamber, a load lock chamber which may be pumped down to create a vacuum therein, and vented to provide an ambient condition therein, is disposed between the factory interface and the transfer chamber. The use of robots in the processing of substrates is essential to processing a large number of substrates through many different types of processing technologies with minimal contamination (e.g., substrate handling contamination), high speed, and accuracy to minimize defects and provide a high throughput system.

In operation, the factory interface robot transfers one or more substrates from a cassette to the interior of the load lock chamber. The load lock chamber is pumped down to create a vacuum therein, and then the transfer chamber robot transfers the substrate(s) from the load lock to the interior of one or more of the process chambers. After the substrate processing sequence is completed, the transfer chamber robot returns the processed substrate to the load lock, the load lock is then vented and the factory interface robot transfers the processed substrate to a cassette for subsequent removal from the processing system. Such substrate processing systems are available from AKT, Inc., a wholly-owned subsidiary of Applied Materials, Inc., of Santa Clara, Calif.

The trend towards increasingly larger substrates and smaller device features requires increasingly precise positional accuracy of the substrate in the various process chambers in order to ensure repetitive device fabrication with low defect rates. Increasing the positional accuracy of substrates throughout the processing system is a challenge. In one example, flat-panel display substrates (e.g., glass substrates) are transferred on an end effector (e.g., a blade or fingers) of a robot to and from the various chambers of the processing system. It is difficult to ensure that flat-panel display substrates align properly with the end effectors of the robots, and once aligned, that the substrate can pass through slots or other obstacles in the load lock or process chambers without collisions due to a shift in alignment (i.e., misalignment) during transfer. A collision may not only chip or crack the flat-panel display substrate, but also create and deposit debris in the load lock or process chambers. Creating such debris may result in processing defects or other damage to the display or subsequently processed displays. Thus, the presence of debris often requires shutting down the system, or a portion thereof, to thoroughly remove the potentially contaminating debris. Moreover, with larger dimension substrates and increased device density, the value of each substrate has greatly increased.

Accordingly, damage to the substrate or yield loss because of substrate misalignment is highly undesirable due to consequential increase in cost and reduction in throughput.

A number of strategies have been employed in order to enhance the positional accuracy (i.e., alignment) of substrates throughout the processing system. For example, a transfer chamber may be equipped with groups of four sensors adjacent the entry of each load lock and process chamber in a sensor arrangement such that the sensors may simultaneously detect the presence of the four corners of a rectangular glass panel for sensing its alignment prior to the robot transferring the substrate into the chamber. Thus, the four sensors are arranged in the base of the transfer chamber at spaced-apart locations such that all four sensors are simultaneously positioned below the four corners of the stationary substrate. Such a disperse arrangement of sensors in front of each of the chambers requires a large number of sensors positioned at many locations across the base of the transfer chamber. Various arrangements of sensors disposed across the base of the transfer chamber have been proposed.

Although conventional sensor arrangements perform satisfactorily, in operation there are several inherent limitations associated with providing these arrangements of sensors. In practice, because the sensors detect the alignment of a single substrate at a time, the transfer chamber may handle/manage only one substrate at a time due to the disperse arrangement of sensors across the base of the transfer chamber. Thus the transfer chamber robot is effectively limited to a single-arm robot which results in reduced throughput of the processing system. Another limitation, which also contributes to a reduced throughput of the processing system, is that the substrate is stationary when positioned over the four sensors during the sensing of its alignment. Still another limitation is at least four sensors are required to sense the alignment of a single substrate. Finally, another limitation is that the four sensors detect substrate defects (e.g., a substrate chip) only at the corners of the substrate.

With the apparatus and method of the present invention, the relatively simple arrangement and fewer number of sensors required to detect the misalignment and/or breakage of a substrate make the present invention easy to implement with relatively low cost.

SUMMARY OF THE INVENTION

The present invention generally provides an apparatus and method incorporating at least two sensors that detect the presence of a substrate. In some embodiments, the apparatus and method includes detecting substrate defects, such as breakage or misalignment, of a moving substrate. In one embodiment, a method for sensing the presence of a moving substrate is described. The method includes moving a substrate relative to a first sensor and a second sensor, and sensing a plurality of first edge portions of the substrate with the first sensor and a plurality of second edge portions of the substrate with the second sensor, the second edge portions being opposite the first edge portions.

In another embodiment, a method for transferring a substrate in a processing system is described. The method includes positioning a substrate on an end effector in a first chamber, moving the substrate through an opening between the first chamber and a second chamber along a substrate travel path, and sensing opposing sides of the substrate travel path using at least two sensors positioned proximate to the opening, each of the at least two sensors defining a beam path that is directed through opposing edge regions of the substrate when at least a portion of an edge region traverses the beam path.

In another embodiment, a method for transferring a substrate in a processing system is described. The method includes positioning a substrate on an end effector in a transfer chamber, moving the substrate through an opening in the transfer chamber along a substrate travel path, sensing opposing sides of the substrate travel path using at least two sensors positioned proximate to the opening, each of the at least two sensors defining a beam path that is directed through the substrate when the substrate traverses the beam path, and detecting the presence of at least one parallel edge region of the substrate as the substrate is moved along the substrate travel path.

In another embodiment, a substrate processing system having an end effector disposed in a first chamber, at least a first sensor and a second sensor, and a controller configured to perform a process is described. The process includes moving a substrate on the end effector along a substrate travel path through an opening between the first chamber and a second chamber, sensing opposing sides of the substrate travel path using the first and second sensors, each of the first and second sensors defining a beam path that is directed through opposing edge regions of the substrate when at least a portion of an edge region traverses the beam path, and monitoring a signal from each of the first and second sensors.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIGS. 3A and 3B are enlarged partial sectional views of the processing system along line 3-3 of FIG. 1 depicting a sensor arrangement within an ambient environment of a factory interface, wherein FIG. 3A shows the sensor arrangement in proximity to a three-slot load lock chamber for detecting substrate breakage and misalignment of substrates transferred into and out of the three slots, and FIG. 3B shows the sensor arrangement in proximity to a four-slot load lock chamber;

FIGS. 4A through 4E are top views of a substrate moving over two sensors and the corresponding sensor signals, wherein FIG. 4A depicts a properly aligned, defect-free substrate, FIGS. 4B and 4D depict a chipped substrate, FIG. 4C depicts a cracked substrate, and FIG. 4E depicts a misaligned substrate.

DETAILED DESCRIPTION

Figure 1:
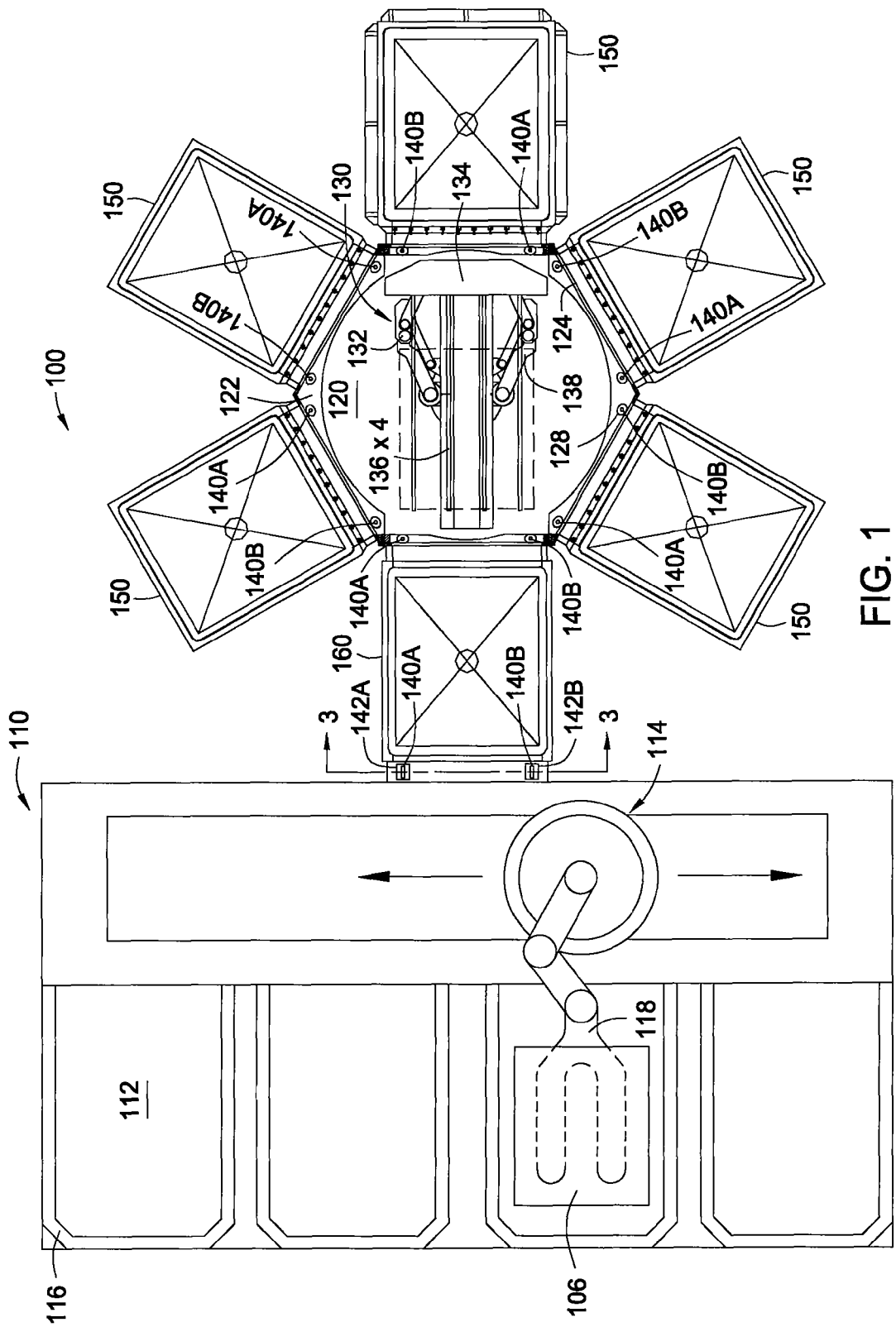
FIG. 1 is a plan view of one embodiment of a processing system including sensors arranged in accordance with one embodiment of the present invention.

The present invention generally provides an apparatus and method incorporating at least two sensors that continuously detect the presence of a substrate chip, crack, and/or misalignment along two parallel edges of a moving substrate. FIG. 1 is a plan view of one embodiment of a processing system 100 suitable for processing large area substrates 106 (e.g., glass or polymer substrates) having a top surface area of greater than about 25,000 cm$^2$, for example, a glass substrate having a top surface area of about 40,000 cm$^2$ (2.2 m×1.9 m). The processing system 100 typically includes a factory interface 110 coupled to a transfer chamber 120 by at least one load lock chamber 160. As depicted in FIG. 1, the load lock chamber 160 is disposed between the factory interface 110 and the transfer chamber 120 to facilitate substrate transfer between a substantially ambient environment maintained in the factory interface 110 and a vacuum environment maintained in the transfer chamber 120.

The factory interface 110 generally includes a plurality of substrate storage cassettes 112 and at least one atmospheric robot 114 (previously referred to as the factory interface robot). The cassettes 112, each of which hold a plurality of substrates, are removably disposed in a plurality of bays 116 formed on typically one side of the factory interface 110. The atmospheric robot 114 is adapted to transfer substrates 106 between the cassettes 112 and the load lock chamber 160. Typically, the factory interface 110 is maintained at or slightly above atmospheric pressure. Filtered air is normally supplied to the interior of the factory interface 110 to minimize the concentration of particles within the factory interface that could lead to particulate contamination of substrate surfaces.

The transfer chamber 120 having a base 122, sidewalls 124, and a top lid 126 (not shown in FIG. 1) houses at least one vacuum robot 130 (previously referred to as the transfer chamber robot) generally disposed on the base 122 of the transfer chamber 120. The transfer chamber 120 defines an evacuable interior volume through which the vacuum robot 130 transfers substrates 106 prior to processing in a process chamber 150 or delivery to the load lock chamber 160. The sidewalls 124 include an opening or port (not shown), adjacent each of the process chambers 150 and load lock chamber 160, through which the substrate 106 may be transferred by the vacuum robot 130 to the interior of each of the chambers 150, 160. Typically, the transfer chamber 120 is maintained at a vacuum condition similar to the sub-atmospheric conditions within the process chambers 150 in order to minimize or eliminate the necessity of adjusting the pressure within the transfer chamber 120 and the pressure within the individual process chambers 150 after each substrate transfer therebetween. The interior of each process chamber 150 is selectively isolated from the interior of the transfer chamber 120 through the use of a slit valve (not shown) to selectively seal the port in the sidewall 124 of the transfer chamber 120 adjacent each of the process chambers 150.

The process chambers 150 are typically bolted to the exterior of the transfer chamber 120. Different process chambers 150 may be attached to the transfer chamber 120 to permit processing a substrate through a processing sequence necessary to form a predefined structure or feature upon the substrate surface. Examples of suitable process chambers 150 include chemical vapor deposition (CVD) chambers, physical vapor deposition (PVD) chambers, ion implantation chambers, etch chambers, orientation chambers, planarization chambers, lithography chambers, as well as other chambers used in processing a substrate. Optionally, one of the process chambers 150 may be a pre-heat chamber that thermally conditions substrates prior to processing in order to enhance throughput of the system 100.

The load lock chamber 160 facilitates transfer of the substrates between the vacuum environment of the transfer chamber 120 and the substantially ambient environment of the factory interface 110 without loss of vacuum within the transfer chamber 120. In a sidewall of the load lock chamber 160 adjacent the factory interface 110, the load lock chamber 160 has one or more entry/exit slots (not shown) through which the atmospheric robot 114 may transfer substrates 106 into and out of the load lock chamber 160. Likewise, the load lock chamber 160 has the same number of entry/exit slots in the opposite sidewall of the load lock chamber 160 through which the vacuum robot 130 may transfer substrates 106 between the interiors of the load lock chamber 160 and the transfer chamber 120. Each of the entry/exit slots of the load lock chamber 160 is selectively sealed by a slit valve (not shown) to isolate the interior of the load lock chamber 160 from the interiors of the factory interface 110 and the transfer chamber 120.

The atmospheric robot 114 and the vacuum robot 130 are equipped with end effectors, such as a blade 118 or fingers 136, respectively, for directly supporting a substrate 106 during transfer. Each of the robots 114, 130 may have one or more end effectors, each coupled to an independently controllable motor (e.g. a dual-arm robot) or, for example, have two end effectors coupled to the robot 114, 130 through a common linkage. As depicted in FIG. 1, vacuum robot 130 is a dual-arm robot having a first arm 132 connected to an upper end effector 134 having fingers 136 for supporting a substrate 106 (designated by the dashed lines) thereon, and a second arm 138 connected to a lower end effector (not shown) with fingers for supporting and moving another substrate within the transfer chamber 120. For increased throughput, the dual-arm vacuum robot 130 may simultaneously transfer two substrates into and out of the various process chambers 150 and to/from the load lock chamber 160. For increased throughput, preferably each of the robots 114, 130 is equipped with two end effectors.

The base 122 of the transfer chamber 120 includes a plurality of view windows 128 disposed proximate the port adjacent each of the process chambers 150 and load lock chamber 160. Proximate each port, at least two sensors 140A, 140B are mounted on or near the exteriors of two windows 128 such that each of the at least two sensors 140A, 140B may view (i.e., sense) an edge portion of the substrate 106 prior to passing through the port. Preferably the sensors 140A, 140B are disposed on the exterior of the windows 128 (i.e., exterior of the transfer chamber) so that the sensors 140A, 140B are isolated from the environment and potentially moderate to high temperatures within the transfer chamber 120. The window 128 may be fabricated of quartz or other material (e.g., glass, plastic) that does not substantially interfere with the detection mechanism of the sensor, for example, a beam of light emitted and reflected back to the sensor 140A (or 140B) through the window 128.

Figure 2:
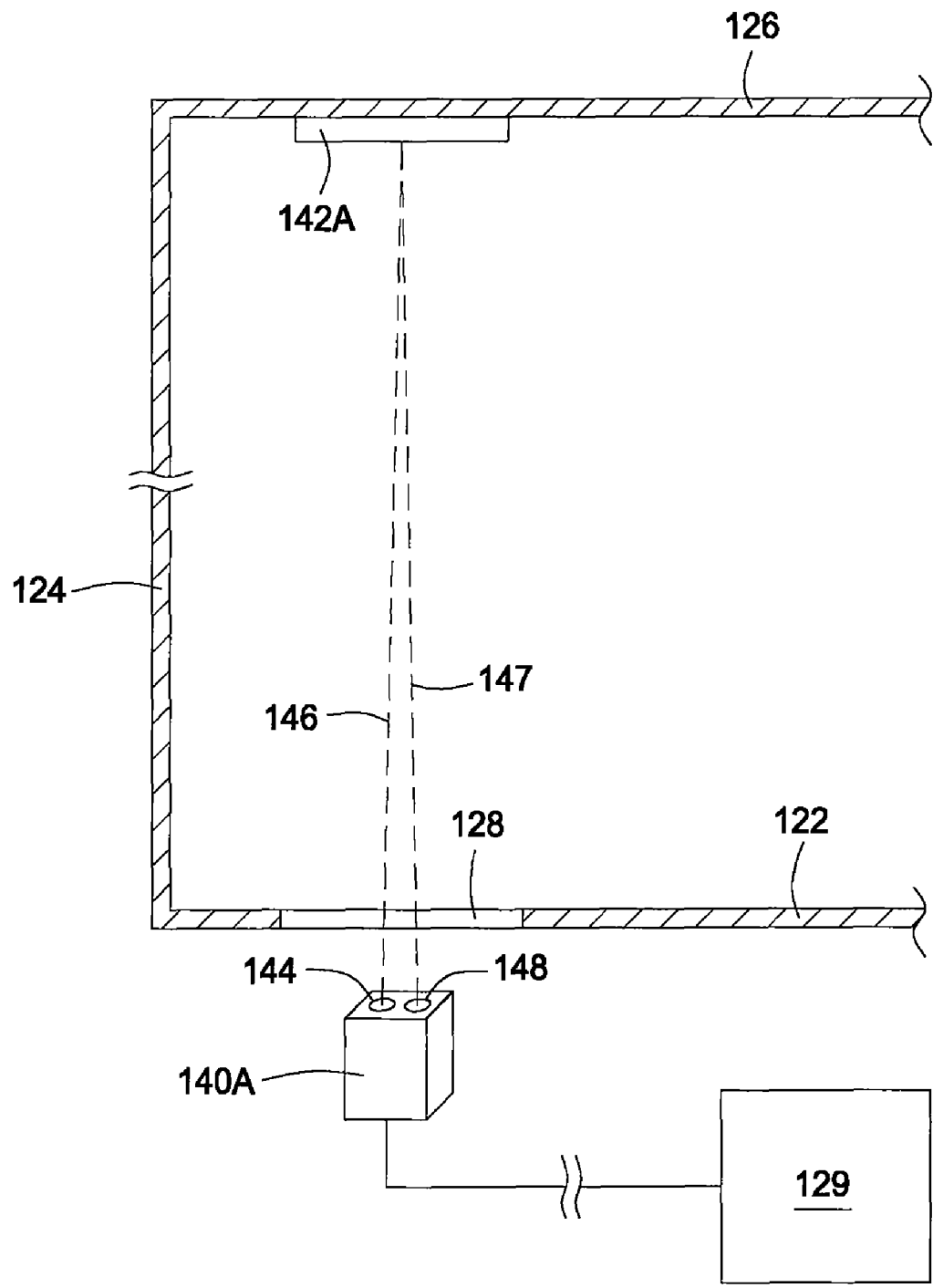
FIG. 2 is an enlarged partial sectional view of the processing system depicting a sensor arrangement in proximity to the entry/exit port of a process chamber for detecting substrate breakage and misalignment before and after processing within the chamber.

FIG. 2 is an enlarged partial sectional side view of the transfer chamber 120, depicting an arrangement of any one of the sensors 140A, 140B disposed proximate the entry/exit port (not shown) in sidewall 124 of the transfer chamber 120 adjacent each of the process chambers 150 and load lock chamber 160. Referring to one of the sensors, for example sensor 140A proximate one of the process chambers 150 of FIG. 1, the sensor 140A includes a transmitter 144 and a receiver 148 generally positioned on or near the exterior of the window 128. The corresponding reflector 142A is mounted on or near an interior side of the transfer chamber lid 126. Because the reflector 142A is essentially a mirror-type device, it is typically less sensitive to temperature and may be operational within a vacuum and moderate temperature environment of the transfer chamber 120. During sensing operation, a beam of light emitted by the transmitter 144 travels through the window 128 along a beam path 146 to the reflector 142A and is reflected by the reflector 142A along another beam path 147 back through the window 128 to the receiver 148. When a glass substrate crosses beam paths 146, 147, the intensity of the beam received by the receiver 148 is attenuated, due to loss of signal from the beam reflections at each glass/air interface encountered along paths 146, 147, indicating the presence of the substrate 106. Sensors 140A, 140B are coupled to a controller 129 configured to continually record, monitor, and compare the beam signals received by the receivers 148 of sensors 140A and 140B. The controller 129 generally includes a CPU, memory and support circuits.

Numerous other sensor configurations may be used to sense the presence of a substrate 106. For example, the reflector 142A may be mounted onto the exterior side of another window (not shown) disposed in the top lid 126 of the transfer chamber 120. Similarly, in another example, the sensor 140A may emit a beam that travels through the window 128 to a second sensor (not shown) positioned on the exterior side of another window (not shown) disposed in the top lid 126 of the transfer chamber 120. Alternatively, other positions of the sensor 140A may be utilized including those within the transfer chamber 120 as long as the environment within the chamber 120 to which the sensor is exposed lies within the operational range (e.g., thermal operating range) of the particular sensor.

Sensor 140A or 140B may include separate emitting and receiving units or may be self-contained such as "thru-beam" and "reflective" sensors or other type of sensing mechanism suitable for detecting the presence of the substrate. In at least one embodiment of the invention, a filter or similar mechanism may be employed to block thermal energy (e.g., infrared wavelengths) from reaching/heating the reflector 142A when, for example, a heated substrate is transferred within the transfer chamber 120, as such heating may affect the reflective properties of certain reflectors. For example, a filter that passes the wavelength or wavelengths emitted by the transmitter 144, but that reflects infrared wavelengths, may be positioned near the reflector 142A.

In one example, the transmitter 144 and receiver 148 may be an Omron® Model No. E32-R16 sensor head having an E3X-DA6 amplifier/transmitter/receiver, which operates at 660 nm, manufactured by Omron® Electronics LLC, of Schaumburg, Illinois. The reflector 142A may be, for example, a Balluff Model No. BOS R-14 reflector manufactured by Balluff, Inc., of Florence, Ky., or an Omron® Model No. E39-R1 reflector. The Omron® E32-R16 sensor has a light emitting diode (LED) that may be used to detect a substrate defect (i.e., breakage or misalignment) having a dimension greater than or equal to about 4 inches. In another example, the transmitter 144 and receiver 148 may be an Omron® Model No. E3C-LR11 laser sensor head operating with amplifiers Model Nos. E3C-LDA11, E3C-LDA21, and a reflector Model No. E39-R12. The Omron® E3C-LR11 laser sensor head may be used to detect substrate defects having a dimension greater than or equal to about 1 mm. Other sensors, reflectors, amplifiers, transmitters, receivers, wavelengths, etc., may be employed. In addition, other sensors having a different sensing mechanism, for example, ultrasonic, may be utilized.

Referring back to FIG. 1, the load lock chamber 160 is also equipped with at least two sensors 140A, 140B proximate the entry/exit slots (not shown) of the load lock adjacent the factory interface 110. The load lock chamber 160 preferably includes one or more vertically-stacked, environmentally-isolatable substrate transfer chambers that may be individually pumped down to hold a vacuum and vented to contain an ambient condition therein. Each of the one or more vertically-stacked environmentally-isolatable chambers has one or more entry/exit slots to allow passage of the substrate therethrough. The arrangement of these sensors 140A, 140B allows detection of substrate breakage and/or substrate misalignment prior to the substrate 106 entering the load lock chamber 160 for subsequent transfer to the transfer chamber 120 and processing. Sensors 140A and 140B are mounted in a spaced-apart relationship such that each of the beams emitted from sensors 140A, 140B pass through a substrate near its parallel edges as the substrate passes the sensors during substrate transfer into or out of a slot of the load lock chamber 160. This spaced-apart sensor arrangement is applicable to any size load lock chamber 160 having any number of slots.

Figure 3A:
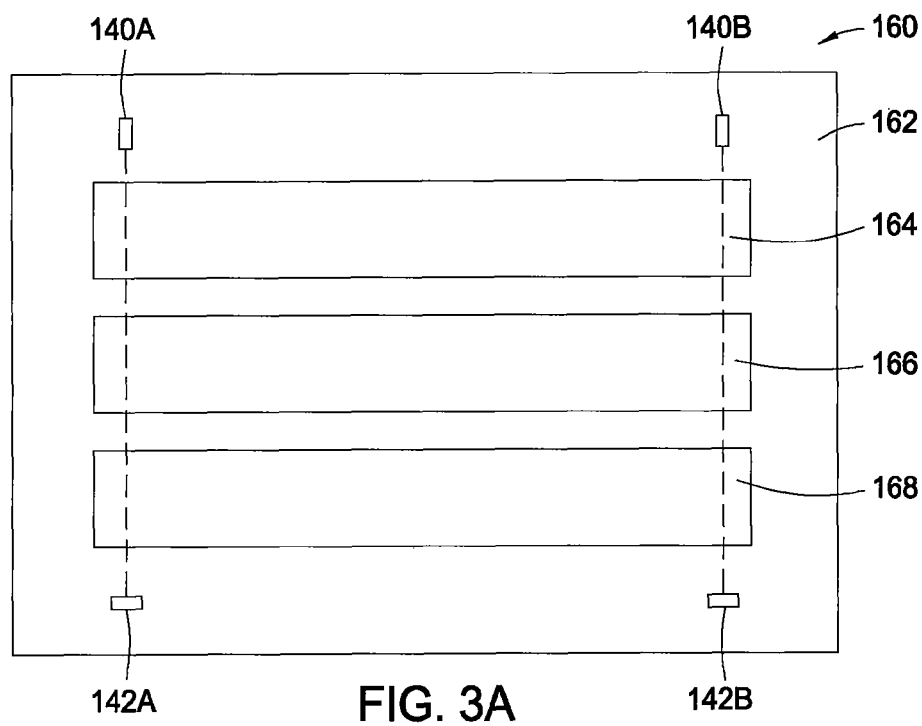
Figure 3B:
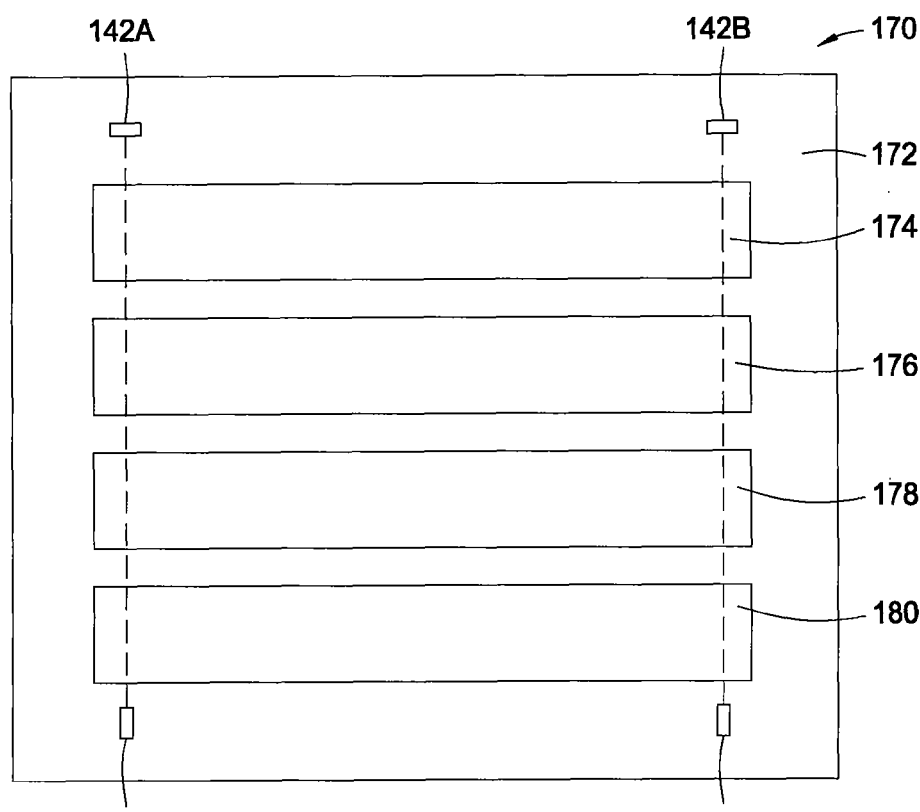
Figure 5:
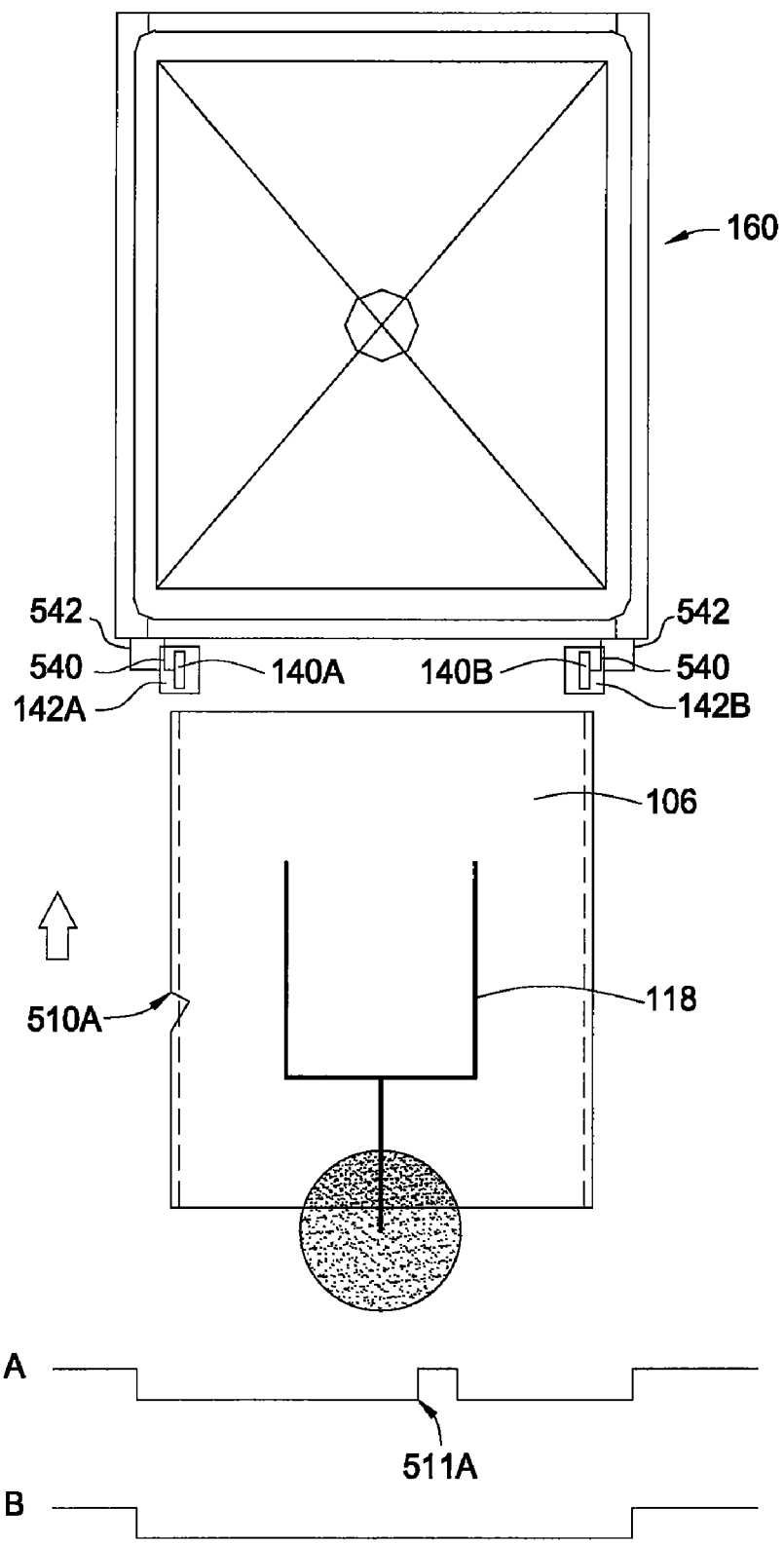
FIG. 5 is a top view of a substrate being transferred on the blade of a factory interface robot under two sensors mounted on the exterior of a load lock chamber and the corresponding sensor signals.

FIGS. 3A and 3B illustrate enlarged sectional side views of the arrangement of the sensors 140A, 140B along line 3-3 of FIG. 1. Each of the sensors 140A, 140B and corresponding reflectors 142A, 142B is generally mounted to the exteriors 162, 172 of the load lock chambers 160, 170, using a fastener such as a bracket (e.g., sensor bracket 540 and reflector bracket 542 as illustrated in FIG. 5) or frame to secure the sensor/reflector in a fixed position. In one example, shown in FIG. 3A, sensors 140A, 140B are mounted above three slots 164, 166, 168 of the load lock chamber 160 and corresponding reflectors 142A, 142B are mounted below the three slots. The load lock chamber 160 having three slots can include one or more environmentally-isolatable chambers such as a triple single-slot load lock chamber (shown in FIG. 3A), a single triple-slot load lock chamber, three vertically stacked load lock chambers each having a single slot, or any other combination of load lock chambers. Likewise, in another example, FIG. 3B illustrates a side view of an arrangement of sensors 140A, 140B proximate a four-slot load lock chamber 170. Sensors 140A, 140B are mounted below the four slots 174, 176, 178, 180 of load lock chamber and corresponding reflectors 142A, 142B are mounted above the four slots. The load lock chamber 170 having four slots can include one or more environmentally-isolatable chambers such as a double dual slot load lock (DDSL) chamber, a quadruple single-slot load lock chamber, a single quadruple-slot load lock chamber, four vertically stacked load lock chambers each having a single slot, or any other combination of load lock chambers. As illustrated in FIGS. 3A and 3B, sensors 140A, 140B may be mounted above or below the slots of the load lock chambers 160, 170.

In FIGS. 3A and 3B, each of the sensors 140A, 140B and corresponding reflectors 142A, 142B operate together as described in FIG. 2, however because no environmental provisions need to be made on the factory interface side it is unnecessary to have a view window for environmentally isolating the sensor As such, the beam of light emitted by the transmitter of sensor 140A (or 140B) travels along a path (indicated by the dashed line) to corresponding reflector 142A (or 142B) and is reflected by the reflector 142A along another path (also indicated by the dashed line; the lateral separation of the paths is not discernible in this view) to the receiver of sensor 140A (or 140B).

In operation, substrate breakage and substrate alignment may be detected when a substrate 106 passes through the beams of light emitted by a pair of sensors 140A, 140B disposed in the transfer chamber 120 proximate the port adjacent one of the process chambers 150 or load lock chamber 160, as illustrated in FIGS. 4A through 4E. The dashed lines near the edges of the substrate 106 indicate the paths near the edges of the substrate where the traveling glass substrate crosses the beams emitted by sensors 140A, 140B located below the substrate.

Figure 4A:
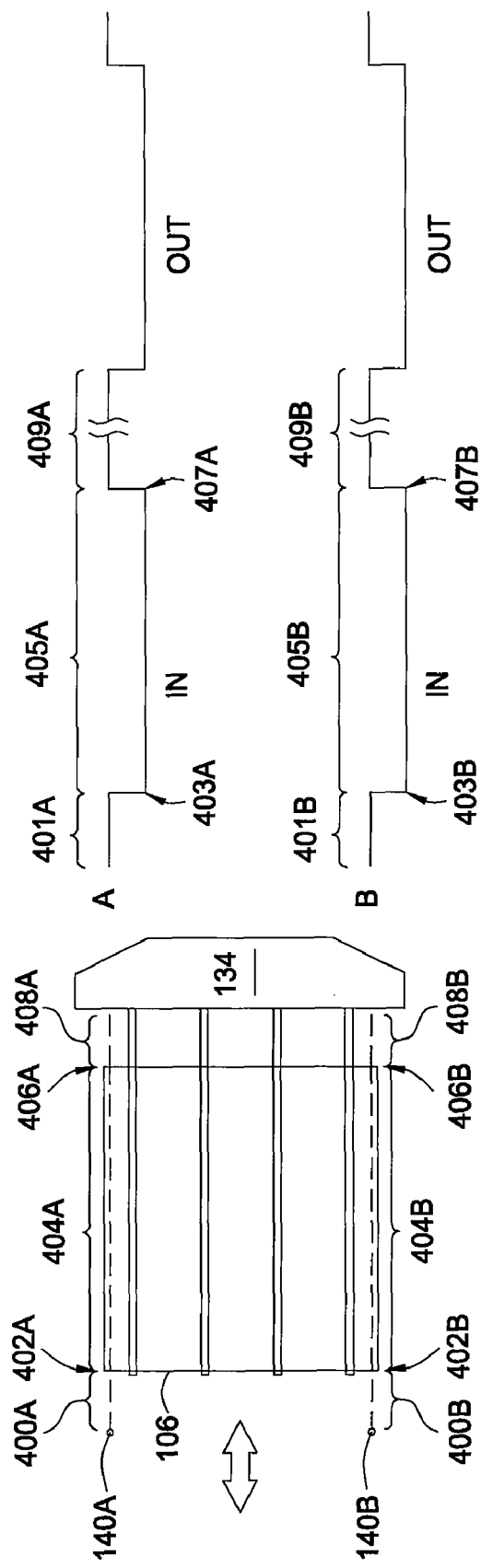

FIG. 4A illustrates a top view of a defect-free (i.e., no chips or cracks) substrate 106 being transferred on an end effector 134 with proper alignment. Prior to sensing the substrate 400A, 400B, the receivers 148 of each of the sensors 140A, 140B detect full beam signals 401A, 401B reflected from the corresponding reflectors 142A, 142B (not shown) located above the substrate. When the substrate 106 enters (i.e., breaks) the beam paths at points 402A, 402B, the beam signals 403A, 403B received by the receivers 148 decrease, due to signal loss at the glass/air interfaces of the substrate 106, indicating the presence of the substrate 106. The beam signals 405A, 405B remain low as the substrate 106 continues to traverse the beams (as indicated by the dashed lines) along the length of the substrate 106. Just as the ends of the substrate 406A, 406B travel past the beams, the beam signals 407A, 407B increase back to their original uninterrupted full beam signals 409A, 409B. Likewise, when a defect-free substrate is transferred back out of the processing chamber 150 (or load lock chamber 160) on an end effector with proper alignment, a similar signal is obtained as the substrate first enters the path of the beams at points 406A, 406B and exits the beams at points 402A, 402B, i.e., in reverse order of the previous description.

Referring to FIGS. 4B, 4C, and 4D, substrate breakage may be detected when a substrate 106 passes through the beams of light emitted by a pair of sensors 140A, 140B. FIG. 4B illustrates a top view of a substrate 106, having an edge chip near one edge of the substrate, being transferred on an end effector 134 with proper alignment. Prior to sensing the substrate 400A, 400B, the receivers 148 of each of the sensors 140A, 140B detect full beam signals 401A, 401B. When the substrate enters the beam paths at points 402A, 402B, the beam signals 403A, 403B received by the receivers 148 decrease, indicating the presence of the substrate 106. The beam signals 405A, 405B remain low as the substrate continues to traverse the beams (as indicated by the dashed lines) along the length of the substrate. However, when the beginning of the substrate chip 410B enters the beam path, the signal increases back to an uninterrupted full beam signal 411B and continues to detect the absence of the substrate 413B over the length of the chip 412B. As the end of the substrate chip 414B passes through the beam, the beam signal 415B decreases again indicating the presence of the substrate 405B until the end of the substrate 406B passes through the beam.

FIG. 4C illustrates a top view of a substrate 106, having a crack near one edge of the substrate, being transferred on an end effector 134 with proper alignment. Prior to sensing the substrate, the receivers 148 of each of the sensors 140A, 140B detect full beam signals 401A, 401B. When the substrate enters the beam paths at points 402A, 402B, the beam signals 403A, 403B received by the receivers 148 decrease, indicating the presence of the substrate 106. The beam signals 405A, 405B remain low as the substrate continues to traverse the beams along the length of the substrate. However, when the beginning of the substrate crack 420B enters the beam path, the signal increases back to an uninterrupted full beam signal 421B and continues to detect the absence of the substrate 423B over the length of the crack 422B. As the end of the substrate crack 424B passes through the beam, the beam signal 425B decreases again indicating the presence of the substrate 405B until the end of the substrate 406B passes through the beam.

FIG. 4D illustrates a top view of a substrate 106, having a corner edge chip near one edge of the substrate, being transferred on an end effector 134 with proper alignment. Prior to sensing the substrate 400A, 400B, the receivers 148 of each of the sensors 140A, 140B detect full beam signals 401A, 429B reflected from the corresponding reflectors 142A, 142B (not shown) located above the substrate. When the substrate enters the beam path of sensor 140A at point 402A, the beam signal 403A decreases indicating the presence of the substrate 106, however, concurrently, the beam path of sensor 140B at point 430B remains uninterrupted due to the presence of the corner chip and the signal 429B remains high. An uninterrupted full signal 429B continues while the beam from sensor 140B traverses the length 432B of the corner chip. Upon reaching the end of the chip 434B, the signal decreases at point 435B indicating the presence of the substrate 437B until the end of the substrate 406B passes through the beam. Due to the substrate chip, sensor 140B detects a shorter length substrate 437B as compared to the length of the substrate 405A sensed by sensor 140A. The length of the substrate, as detected by sensor 140B, is shortened by distance 432B which results in a delay 433B before the substrate 106 is detected at point 435B.

FIG. 4E illustrates a top view of a substrate 106 being transferred on an end effector 134 with a misalignment. Prior to sensing the substrate 442A, 442B, the receivers 148 of each of the sensors 140A, 140B detect full beam signals 443A, 443B reflected from the corresponding reflectors 142A, 142B (not shown) located above the substrate. When the substrate enters the beam path of sensor 140A at point 444A, the beam signal 445A received by the corresponding receiver 148 decreases indicating the presence of the substrate 106, however, concurrently, the beam path of sensor 140B remains uninterrupted for an additional length 444B due to the shift in alignment (i.e., misalignment). The uninterrupted full signal 443B continues while the beam traverses the length of the misalignment 444B. When the substrate breaks the beam path of sensor 140B at point 446B, the signal 447B decreases indicating the presence of the substrate 106. Afterwards, at point 448A, the beam path of sensor 140A detects the end of the substrate and the corresponding receiver 148 increases to full strength 449A, whereas the beam path of sensor 140B continues to detect the presence of the substrate until the end of the substrate at 450B where the signal 451B increases back to its original uninterrupted full beam signal 453B. Due to the misalignment, both sensors 140A and 140B detect a shorter length substrate 447A, 449B. The length of the substrate as detected by sensor 140A is shortened by distance 450A which results in an early increase in signal at point 449A as compared to a properly aligned substrate. Likewise, the length of the substrate 106 as detected by sensor 140B is shortened by distance 444B which results in a delay before the substrate is detected at point 447B.

The sensor arrangement of the present invention advantageously allows detection of breakage (e.g., chip, crack) and misalignment of a substrate while the substrate is supported and transferred on a dual-arm robot. The use of a dual-arm robot provides increased throughput of the processing system. Another advantage, which contributes to an increased throughput, is the ability to detect misalignment and breakage of a substrate while it is moving, even at high transfer speeds (e.g., 1000 mm/s) on an end effector of a robot. Still another advantage of the present invention is that as few as two sensors are required to detect breakage and misalignment of a substrate. Finally, another advantage of the present invention is the ability to detect misalignment and breakage of a substrate along the entire length of a substrate as the substrate moves past the sensors. Furthermore, detection of substrate misalignment and breakage may be performed during normal robotic transfer operations (i.e., in-situ), which obviates the need for additional or unnecessary robotic movements (including stops and starts to provide a stationary substrate) for the purpose of sensing a substrate.

One advantage of the present invention is substrate breakage and misalignment may be detected as a substrate is moving, even at high transfer speeds. During sensing for defects, the substrate is preferably moving (e.g., being transferred on an end effector of a robot) at a transfer speed in a range of about 100 mm/s to about 2000 mm/s. The smallest size substrate chip, crack, or the smallest degree of substrate misalignment that may be detected by an LED or laser system is dependent upon both the beam size (i.e., the spot size or diameter) of the emitted beam when it impinges upon a top or bottom surface of the substrate, and the transfer speed of the substrate. In general, the smaller the emitted beam diameter, the finer or smaller the defect feature that may be detected. For example, a suitable laser sensor may emit a laser beam having a diameter in a range of about 0.5 mm to about 3 mm. However, in order to detect substrate chips or cracks having a size as small as 1 mm (i.e., greater than about 1 mm), for example, the diameter of the emitted laser beam when the beam impinges a surface of the substrate is preferably less than about 1 mm. Thus, the substrate is positioned within a working distance of the particular sensor used in order to ensure the impinging beam diameter on a top or bottom surface of the substrate is small enough to detect the smallest size substrate chip, crack or misalignment that needs to be detected.

The size of defect that may be detected by a laser system is also influenced by the transfer speed of the substrate as a result of the vibration a moving substrate invariably experiences, for example, while being transferred on an end effector of a robot. Generally, the faster the transfer speed or velocity of the substrate, the more vibration a substrate experiences. Vibration tends to cause the substrate edges to move upwards and downwards. As a result, the sensor is positioned such that the emitted beam impinges upon the top or bottom surface of the moving substrate at a nominal distance inward from the edge of the substrate. Otherwise, a beam directed at the very edge of a vibrating substrate would invariably sense an absence of substrate each time the substrate edge moves in and out of the beam due to vibration. Thus, the more a substrate vibrates, the further inward from an edge of the substrate the incident beam is directed. For example, a laser sensor having an emitted beam diameter in a range of about 0.5 mm to about 3 mm and a substrate moving at a transfer speed in a range of about 100 mm/s to about 2000 mm/s, the laser beam may be directed such that the impinging beam on the top (or bottom) surface of the substrate is positioned at a distance in a range of about 1 mm to about 10 mm from the edge of the substrate.

EXAMPLES

In one example, two Omron® Model No. E3C-LR11 laser sensors having a beam diameter of less than about 0.8 mm at working distances up to about 1000 mm (i.e., working distances of less than about 40 inches) is used to sense a substrate along its two parallel edges as the substrate, supported on an end effector of a dual-arm robot, passes the sensors. At a substrate transfer speed of about 1000 mm/s, defects having a size of about 3 mm or greater were detectable. The center of the impinging beam from each sensor was positioned at a distance of about 3 mm inward from the edges of the substrate. At a substrate transfer speed of about 100 mm/s, defects having a size of about 1 mm or greater were detectable, and at a substrate transfer speed of about 2000 mm/s, defects having a size of about 10 mm or greater were detectable. Thus, the two impinging beams for sensing a substrate being transferred at a speed in a range of about 100 mm/s to about 2000 mm/s are preferably positioned at distances in a range of about 1 mm to about 10 mm, respectively, inward from the substrate edges. Using the laser to detect defect features having a size smaller than 3 mm may be accomplished by decreasing the velocity of the substrate. Decreasing the substrate velocity decreases the vibration the substrate experiences and as a result smaller defects may be resolved. Conversely, increasing the substrate velocity increases the vibration of the substrate and the larger the detectable defect.

In another example, two Omron® Model No. E32-R16 LED sensors and two Balluff Model No. BOS R-14 reflectors are used to sense a substrate along its two edges as the substrate supported on an end effector of a robot is transferred into a three-slot load lock chamber in a configuration as depicted in FIG. 3A. The LED sensor mounted above the top slot emits a beam that travels along a beam path to the reflector positioned within the working distance of the LED sensor. At a substrate transfer speed of about 1000 mm/s, substrate chips having a size of about 4 inches or greater and misalignment of greater than or equal to about 2.6 degrees were detectable on substrates transferred into each of the slots.

In still another example, two Omron® Model No. E3C-LR11 laser sensors and Omron® odel No. E39-R12 reflectors are used to sense a substrate along its two edges as the substrate supported on an end effector of a robot is transferred into a DDSL chamber in a configuration as depicted in FIG. 3B. The laser sensor mounted below the bottom slot emits a beam that travels along a beam path past each of the four slots to a reflector mounted within the working distance of the laser sensor. Substrate chips of about 3 mm or greater and substrate misalignment of about 0.18 degrees or greater were detectable on substrates transferred at a velocity of about 1000 mm/s into each of the four slots of the load lock chamber.

In practice, each of the pair of sensors 140A, 140B (and corresponding reflectors) positioned near each of the entry/exit ports of the process chambers 150 and load lock chamber 160 detect substrate breakage and misalignment before and after processing within the process chamber or passing through the load lock chamber. Upon sensing breakage or misalignment of a substrate, the controller coupled to the sensors may be configured to trigger an alarm and immediately stop the motion/transfer of the defective substrate so as to allow breakage or misalignment to be remedied by, for example, determining the cause of the substrate breakage or misalignment, replacing the chipped/cracked substrate, and correcting the alignment of the misaligned substrate. Sometimes the detection of a chipped substrate requires opening up the transfer chamber and/or a processing chamber to thoroughly clean any potentially contaminating debris generated by the chip. The sensor arrangement of the present invention allows for early detection of substrate defects which minimizes downtime and thus increases the overall throughput of the system 100. For example, FIG. 5 illustrates a top view of a substrate 106 having an edge chip near one edge of the substrate, being transferred on an end effector 118 of factory interface robot 114 to load lock chamber 160. The dashed lines near the edges of the substrate indicate the path where the traveling substrate will cross the beams emitted by sensors 140A, 140B positioned above the substrate 106 and the corresponding signals A, B, respectively. At the onset of sensing a substrate chip at point 510A, the corresponding signal 511A increases and the controller immediately stops the end effector 118 from traveling further into the load lock chamber 160. The chipped substrate may then be evaluated to determine whether or not it is desirable to further process the substrate 106.

Although the illustrative detection of substrate breakage and misalignment uses at least two sensors 140A, 140B to sense the entire length of a substrate near its edges provides information about the length of a chip and/or the degree of misalignment, additional sensors may be utilized to sense the length of an interior portion of the substrate 106 to provide additional information. For example, additional sensors positioned between sensors 140A and 140B may provide additional information as to the dimensions of a substrate chip (e.g. lateral depth or width of the chip) or degree of misalignment (e.g., extent of shift in alignment). Moreover, additional pairs of sensors 140A, 140B may be positioned at other locations throughout the processing system 100 where the sensors 140A, 140B may be used to sense a single substrate at any one time. The sensors may be mounted to essentially any interior and/or exterior surfaces of the processing system over (or under) a travel path of a moving substrate. Accordingly, there may be more than two view windows proximate each port of the transfer chamber 120. For example, the base 122 may have any number of view windows to accommodate additional sensors and/or to accommodate different spaced-apart arrangements of sensors 140A, 140B for sensing different size substrates in order to direct the beams emitted from the sensors 140A, 140B such that they cross a passing substrate near at least two edges of the substrate. Alternatively, instead of using a plurality of view windows 128 proximate a port adjacent a chamber, a single long view window, for example a long rectangular-shaped window, approximating the length of the port may be installed in the base 122 such that a plurality of sensors mounted near the exterior of the single long view window may sense a passing substrate. Finally, the illustrative detection of substrate breakage and misalignment is described with reference to the exemplary processing system 100, however the description is one of illustration, and accordingly, the method may be practiced wherever detection of breakage or misalignment of a moving substrate is desired.

While the foregoing is directed to embodiments of the present invention, other and further embodiments of the invention may be devised without departing from the basic scope thereof, and the scope thereof is determined by the claims that follow.

The invention claimed is:

1. A method for sensing the presence of a moving substrate, comprising:

moving a rectangular substrate in a linear travel path relative to a first sensor and a second sensor positioned on opposing sides of the linear travel path, the positions of the first sensor and second sensor selected to sense opposing edges of the rectangular substrate along the linear travel path; and sensing a plurality of first edge portions of the rectangular substrate with the first sensor and a plurality of second edge portions of the rectangular substrate with the second sensor as the opposing edges move parallel to the linear travel path, the second edge portions and the first edge portions being immediately inward of the opposing edges of the rectangular substrate.

2. The method of claim 1, wherein each of the first sensor and the second sensor defines an optical beam path that continuously senses the linear travel path.

3. The method of claim 2, wherein each optical beam path impinges at least one of a top surface or a bottom surface of the substrate during at least a portion of the time during which the substrate is moving relative to the first and second sensors.

4. The method of claim 3, wherein each optical beam path is orthogonal to the at least one of the top surface or the bottom surface that it impinges while the substrate is moving relative to the first and second sensors.

5. The method of claim 3, wherein each optical beam path passes through the at least one of the top surface or the bottom surface that it impinges.

6. The method of claim 1, further comprising:

continuously monitoring a light beam from each of the first sensor and the second sensor to determine an optical intensity of each light beam.

7. The method of claim 6, further comprising:

detecting a crack, a chip, or a defect in the substrate by determining if the optical intensity of the light beam from at least one of the first sensor or the second sensor is greater than the optical intensity of the light beam from the at least one of the first sensor or the second sensor in the absence of the crack, the chip, or the defect in the substrate.

8. The method of claim 6, wherein the optical intensity of the light beam from at least one of the first sensor or the second sensor is not substantially attenuated when the substrate is misaligned.

9. The method of claim 6, wherein (i) the optical intensity of the light beam from the first sensor is attenuated, and (ii) the optical intensity of the light beam from the second sensor is greater than the optical intensity of the light beam from the first sensor when the substrate is misaligned.

10. The method of claim 6, further comprising:

providing an alarm to a user when the optical intensity of the light beam from at least one of the first sensor or second sensor is not attenuated by the substrate.

11. A substrate processing system having an end effector disposed in a first chamber, at least a first sensor and a second sensor, and a controller configured to perform a process, the process including:

moving a rectangular substrate having parallel opposing edges on the end effector along a linear substrate travel path through an opening between the first chamber and a second chamber, each edge having an orientation parallel to the travel path and an edge region immediately inwards of the edge, the first sensor and the second sensor positioned adjacent each side of the opening and spaced apart a distance to simultaneously sense defects in the opposing edge regions;

sensing opposing edge regions of the rectangular substrate using the first sensor and the second sensor, each of the first sensor and the second sensor defining a beam path that is directed through parallel edge regions of the rectangular substrate when at least a portion of the edge region inward of parallel opposing edges of the rectangular substrate traverses the beam path; and monitoring a signal from each of the first sensor and the second sensor as the rectangular substrate traverses the beam path.

12. The system of claim 11, wherein the monitoring the signal comprises:

monitoring an optical intensity of each beam path to determine an attenuation of each beam path.

13. The system of claim 12, further comprising:

providing an alarm to a user when the optical intensity of the beam path from the first sensor is greater than the optical intensity of the beam path from the second sensor to indicate an absence of the rectangular substrate proximate to the first sensor.

14. An apparatus for detecting substrate defects, comprising:

a robot having an end effector configured to retain a rectangular substrate, the end effector operable to move the substrate along a linear substrate travel path and through an opening in a chamber;

a first sensor positioned adjacent the opening in the chamber;

a second sensor positioned on an opposing side of the opening, each of the first sensor and the second sensor defining an optical beam path positioned to continuously intersect a linear substrate travel path and sense a plurality of first edge portions of a rectangular substrate and a plurality of second edge portions of the rectangular substrate as the rectangular substrate moves along the travel path, the first edge portions being opposite the second edge portions and inward of parallel edges of the rectangular substrate, the first sensor and the second sensor spaced apart a distance to simultaneously sense defects in the opposing edge regions; and a controller that monitors the optical beam path of each of the first sensor and second sensor as the rectangular substrate moves along the travel path.

15. The apparatus of claim 14, wherein each of the first sensor and the second sensor are positioned proximate a passage of a chamber to sense the rectangular substrate prior to entering the passage or after the rectangular substrate exits the passage.

16. The apparatus of claim 14, wherein the robot further comprises:

a first arm connected to a first end effector configured to support the rectangular substrate and transfer the rectangular substrate through the optical beam path of each of the first sensor and the second sensor; and a second arm connected to a second end effector configured to support and move another rectangular substrate.

17. The apparatus of claim 14, wherein each of the first sensor and second sensor comprises:

a transmitter;

a receiver; and a reflector, the transmitter and receiver positioned below an edge region of the rectangular substrate and the reflector is positioned above the edge region of the rectangular substrate.

18. The apparatus of claim 17, wherein the transmitter is a laser configured to emit a laser beam of light having a diameter less than about 3 millimeters when the laser beam of light impinges upon a top or bottom surface of the rectangular substrate.

19. The apparatus of claim 14, wherein the optical beam path of each of the first sensor and the second sensor impinges at least one of a top surface or a bottom surface of the rectangular substrate during at least a portion of the time during which the rectangular substrate is moving relative to the first and second sensors.

20. The apparatus of claim 19, wherein the optical beam path of each of the first sensor and the second sensor is orthogonal to the at least one of the top surface or the bottom surface that it impinges while the rectangular substrate is moving relative to the first and second sensors.

21. An apparatus for detecting substrate breakage and misalignment along a substrate transfer path, comprising:
a transfer chamber;
a movable end effector within the transfer chamber having a support surface operable to support a rectangular substrate thereon and movable within a range of motion that defines at least a portion of a substrate transfer path;
a sensor system including at least two sensors positioned adjacent the substrate transfer path in a configuration such that an optical beam path of each of the at least two sensors sense at least two parallel edges of the rectangular substrate as the rectangular substrate moves along the substrate transfer path, the at least two sensors positioned adjacent each side of the substrate transfer path and spaced apart a distance to simultaneously sense defects in opposing edges of the rectangular substrate which are in a parallel orientation with the substrate transfer path; and
a controller that monitors the optical beam path of each of the at least two sensors as the rectangular substrate moves along the substrate transfer path.

22. The apparatus of claim 21, wherein the at least two sensors are coupled to the transfer chamber proximate a passage of the transfer chamber to sense the rectangular substrate prior to entering the passage or after the rectangular substrate exits the passage.

23. The apparatus of claim 21, wherein the at least two sensors are coupled to an adjacent chamber proximate a passage of the adjacent chamber to sense the rectangular substrate prior to entering the passage or after the rectangular substrate exits the passage.

24. The apparatus of claim 23, wherein the adjacent chamber is a load lock chamber.

25. The apparatus of claim 23, wherein the adjacent chamber is a processing chamber.

26. The apparatus of claim 21, wherein the at least two sensors comprise a first sensor and a second sensor, the first sensor positioned on a first side of the substrate travel path and the second sensor positioned on an opposing side of the substrate travel path.

27. The apparatus of claim 26, wherein the optical beam path of each of the first sensor and the second sensor impinges at least one of a top surface or a bottom surface of the rectangular substrate during at least a portion of the time during which the rectangular substrate is moving relative to the first sensor and the second sensor.

28. The apparatus of claim 27, wherein the optical beam path of each of the first sensor and the second sensor is orthogonal to the at least one of the top surface or the bottom surface that the optical beam path impinges while the rectangular substrate is moving relative to the first and second sensors.

29. The apparatus of claim 27, wherein the optical beam path of each of the first sensor and the second sensor passes through the at least one of the top surface or the bottom surface that the optical beam path impinges.

* * * * *